(12) United States Patent
Pearl, Jr. et al.

(10) Patent No.: US 10,317,567 B2
(45) Date of Patent: Jun. 11, 2019

(54) THREE-DIMENSIONAL WAVEGUIDE SENSORS FOR SAMPLE ANALYSIS

(71) Applicant: Halliburton Energy Services, Inc., Houston, TX (US)

(72) Inventors: William Cecil Pearl, Jr., Houston, TX (US); Megan Renee Pearl, Houston, TX (US); David L. Perkins, The Woodlands, TX (US); Neal G. Skinner, Lewisville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/102,486

(22) Filed: Aug. 13, 2018

(65) Prior Publication Data

US 2018/0364391 A1    Dec. 20, 2018

Related U.S. Application Data

(62) Division of application No. 14/781,053, filed as application No. PCT/US2014/058818 on Oct. 2, 2014, now Pat. No. 10,073,188.

(51) Int. Cl.

| G01N 21/77 | (2006.01) |
| G01V 8/16 | (2006.01) |
| G01N 21/45 | (2006.01) |
| G02B 1/10 | (2015.01) |
| G02B 6/10 | (2006.01) |
| G01B 9/02 | (2006.01) |

(Continued)

(52) U.S. Cl.
CPC ........... *G01V 8/16* (2013.01); *G01B 9/02049* (2013.01); *G01N 21/45* (2013.01); *G01N 21/7703* (2013.01); *G02B 1/10* (2013.01);

*G02B 6/00* (2013.01); *G02B 6/10* (2013.01); *G02B 6/29352* (2013.01); *G01N 2021/458* (2013.01)

(58) Field of Classification Search
None
See application file for complete search history.

(56) References Cited

U.S. PATENT DOCUMENTS

| 4,877,747 A | 10/1989 | Stewart |
| 5,623,561 A | 4/1997 | Hartman |

(Continued)

FOREIGN PATENT DOCUMENTS

| WO | WO-2009/115847 A1 | 9/2009 |
| WO | WO-2016/053340 A1 | 4/2016 |

OTHER PUBLICATIONS

Puyol et al., Improved Integrated Waveguide Absorbance Optodes for Ion-Selective Sensing, Anal. Chem. 2002, 74, 3354-3361.

(Continued)

*Primary Examiner* — Chad H Smith
(74) *Attorney, Agent, or Firm* — Gilliam IP PLLC

(57) ABSTRACT

Systems and methods for measuring a characteristic of a fluid are provided. The system includes a plurality of waveguides embedded in a substrate, and an exposed surface of the substrate comprising a portion of a side surface of at least one of the plurality of waveguides. The system also includes a sensitized coating in the at least one of the plurality of waveguides. The exposed surface is curved in a direction perpendicular to a light propagation in the waveguide. A method of fabricating a system as above is also provided.

20 Claims, 11 Drawing Sheets

(51) Int. Cl.
*G02B 6/293* (2006.01)
*G02B 6/00* (2006.01)

(56) References Cited

U.S. PATENT DOCUMENTS

| | | | |
|---|---|---|---|
| 5,690,894 | A | 11/1997 | Pinkel et al. |
| 5,786,439 | A | 7/1998 | Van Antwerp et al. |
| 5,846,842 | A | 12/1998 | Herron et al. |
| 5,917,966 | A | 6/1999 | Beuhler et al. |
| 6,429,023 | B1 | 8/2002 | Gharavi |
| 6,493,090 | B1 | 12/2002 | Lading et al. |
| 6,545,759 | B1 | 4/2003 | Hartman |
| 6,728,429 | B1 | 4/2004 | Melman et al. |
| 7,583,865 | B2 | 9/2009 | Berger |
| 7,820,983 | B2 * | 10/2010 | Lundquist .......... G01N 21/6452 250/458.1 |
| 7,936,448 | B2 | 5/2011 | Albuquerque et al. |
| 8,445,841 | B2 | 5/2013 | Szobota et al. |
| 2005/0052655 | A1 | 3/2005 | Jones et al. |
| 2008/0002202 | A1 | 1/2008 | Hall et al. |
| 2010/0234684 | A1 | 9/2010 | Blume et al. |
| 2013/0197327 | A1 | 8/2013 | Chen et al. |

OTHER PUBLICATIONS

Wolfbeis, Otto S., Fiber-Optic Chemical Sensors and Biosensors, Anal. Chem. 2004, 76, 3269-3284.

Hernaez et al., Study of Superhydrophilic Nanoparticle-Based Ultra-Thin Films Towards the Development of Optical Fiber Humidity Sensors, International Journal on Smart Sensing and Intelligent Systems, vol. 2, No. 1, Mar. 2009.

Mukundan, et al., Quantitative Multiplex Detection of Pathogen Biomarkers on Multichannel Waveguides, Anal. Chem. 2010, 82, 136-144.

Mukundan et al., Waveguide-Based Biosensors for Pathogen Detection, Sensors, 2009, 9, 5783-5809.

International Search Report and Written Opinion for PCT/US2014/058818 dated Jul. 3, 2015.

* cited by examiner

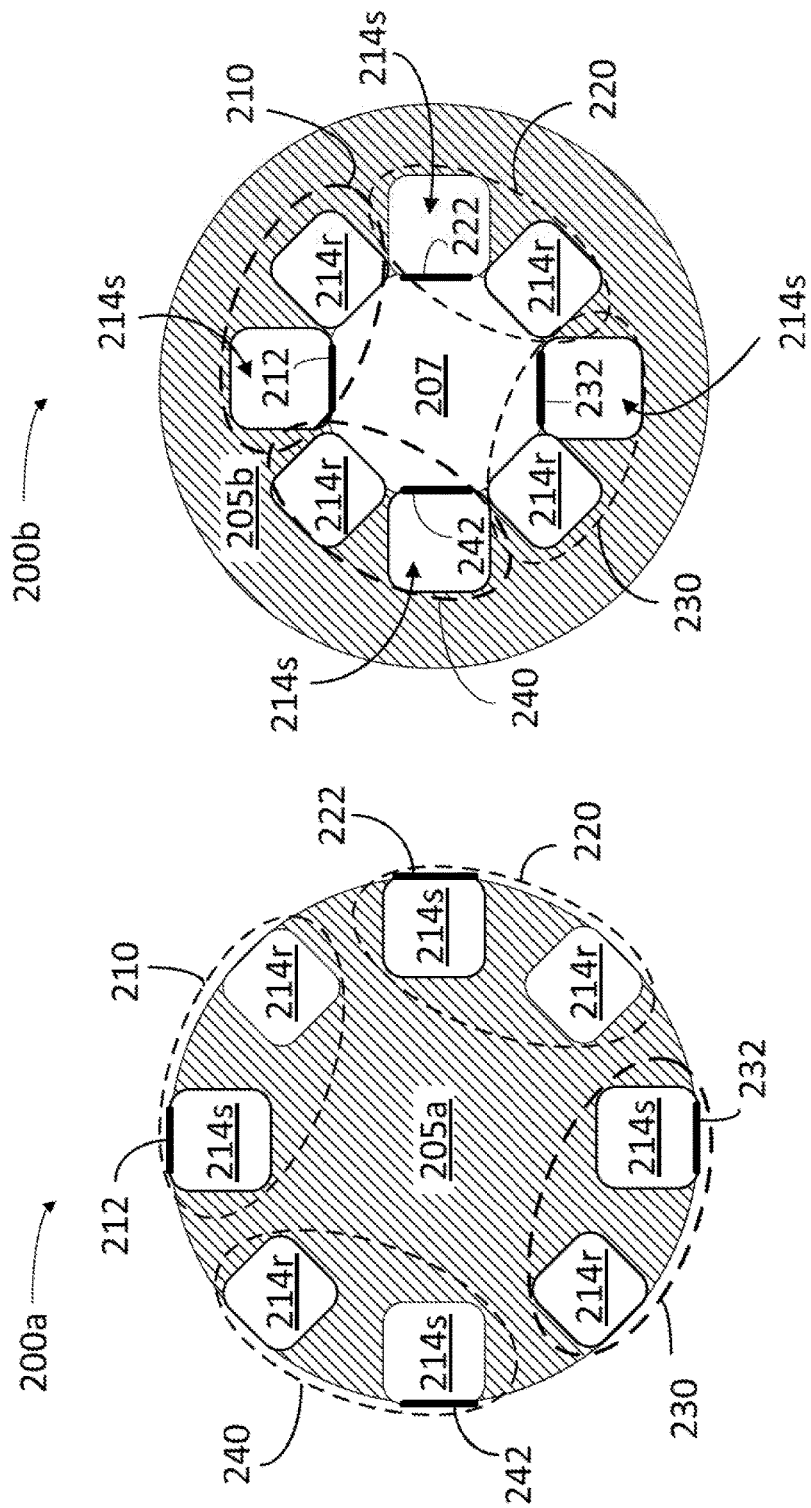

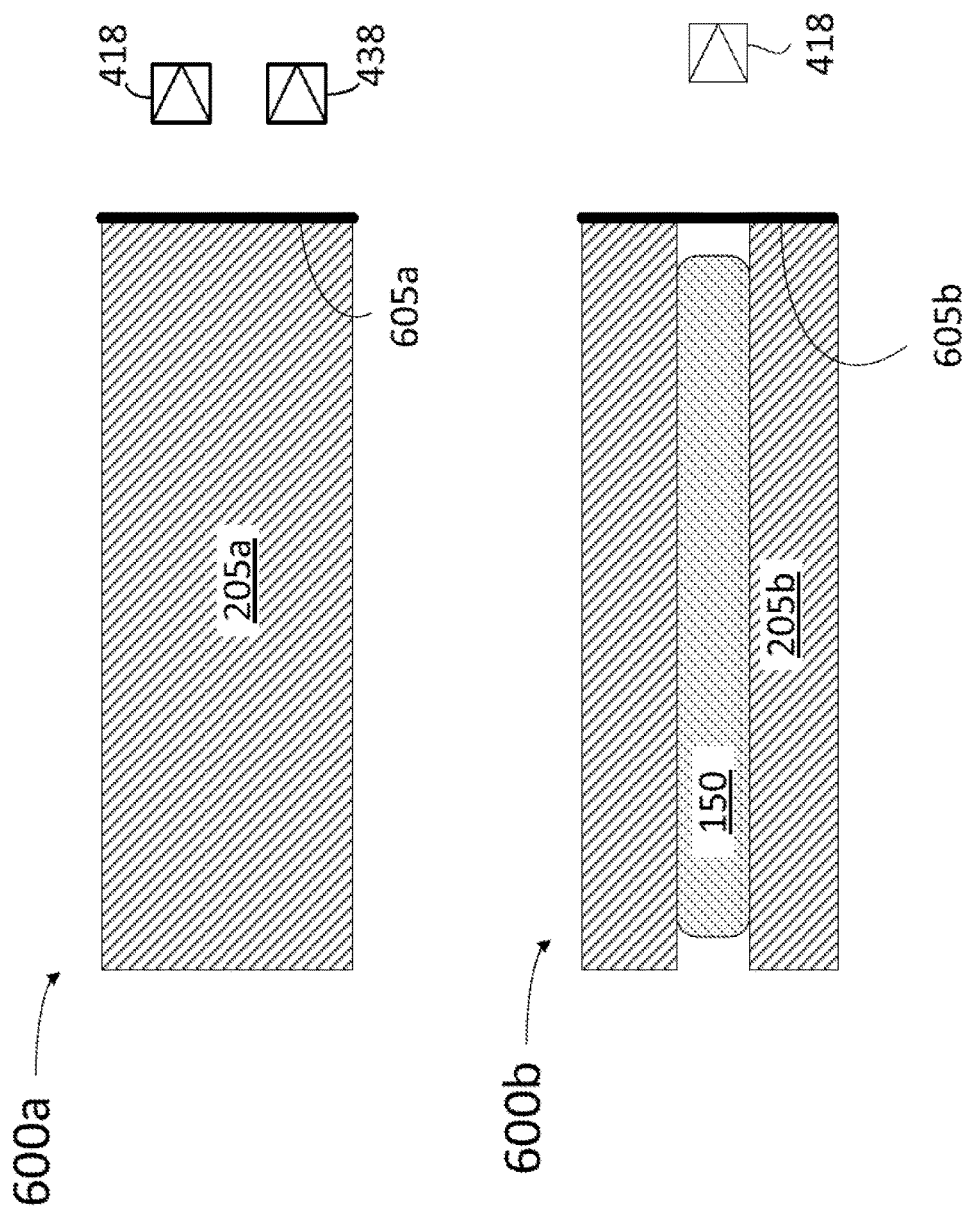

THREE-DIMENSIONAL WAVEGUIDE SENSORS FOR SAMPLE ANALYSIS

CROSS-REFERENCE TO RELATED APPLICATIONS

The present application claims the benefit of priority under 35 U.S.C. § 120 as a divisional from U.S. patent application Ser. No. 14/781,053, entitled "THREE-DIMENSIONAL WAVEGUIDE SENSORS FOR SAMPLE ANALYSIS," filed on Sep. 29, 2015, which is the national stage entry of International Application No. PCT/US2014/058818, entitled "THREE-DIMENSIONAL WAVEGUIDE SENSORS FOR SAMPLE ANALYSIS," filed on Oct. 2, 2014, the disclosures of which are hereby incorporated by reference in their entirety for all purposes.

BACKGROUND

The present disclosure relates to sensors incorporating waveguides in a three-dimensional (3D) substrate for use in the oil and gas industry. More specifically, the present disclosure relates to interferometry-based chemical sensors to measure fluid samples relevant in the oil and gas industry.

Chemical sensors using planar waveguide arrays in a Mach-Zehnder interferometer configuration have gained popularity for their high sensitivity. However, planar geometries are incompatible with the relatively large and circular cross-sections of optical fibers used to reach the depths of some wellbores in oil and gas exploration and extraction operations. In such downhole environments, the fragile complexion of planar waveguide arrays becomes a hindrance, as alignment procedures need to be enhanced. Also, planar waveguide arrays are more susceptible to stress, strain, high temperatures, and high pressures commonly encountered in downhole applications.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2A illustrates a cross-sectional view of a sensor incorporating waveguides in a 3D substrate, according to some embodiments.

FIG. 2B illustrates a cross-sectional view of a sensor incorporating waveguides in a 3D substrate, according to some embodiments.

FIG. 6C illustrates a side view of the sensors of FIGS. 6A and 6B, according to some embodiments.

DETAILED DESCRIPTION

Figure 1:
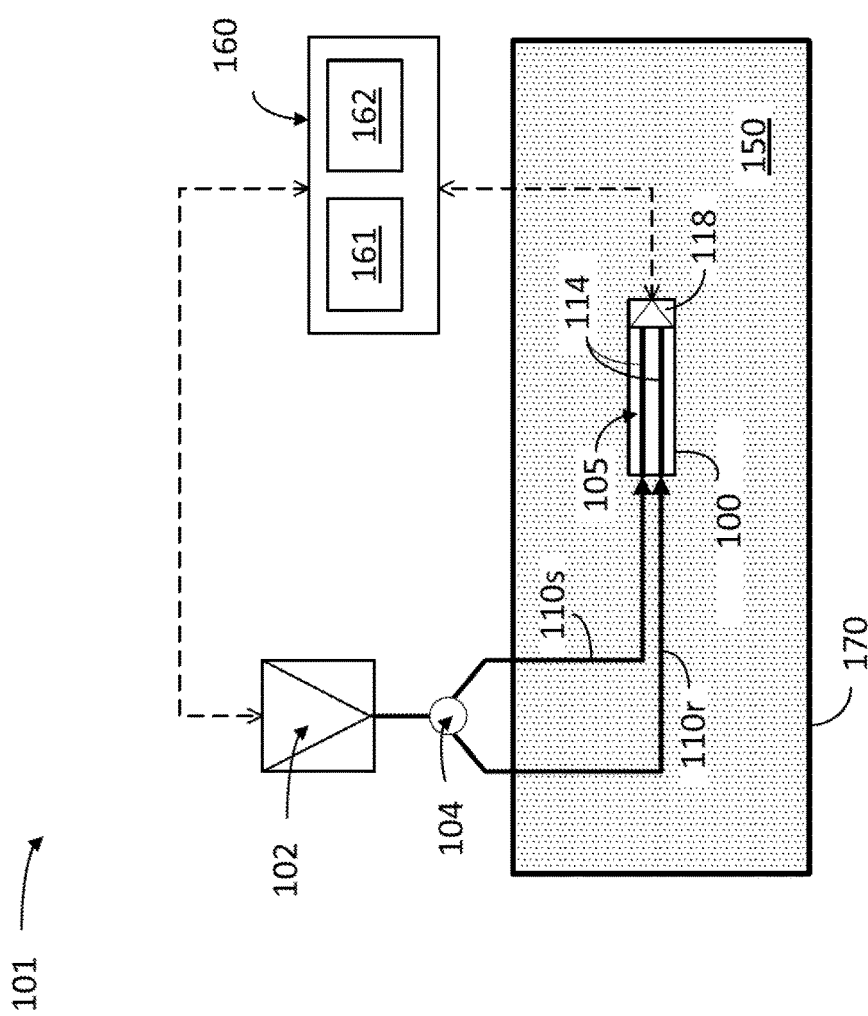
FIG. 1 illustrates a measurement system including a sensor incorporating waveguides in a 3D substrate, according to some embodiments.

The present disclosure relates to sensors incorporating waveguides in a three-dimensional (3D) substrate for use in the oil and gas industry. More specifically, the present disclosure relates to interferometry-based sensors to measure fluid samples relevant in the oils and gas industry.

Measurement of fluid samples, as disclosed herein, includes measuring a characteristic or analyte of relevance in the sample. Embodiments as disclosed herein make use of the optical interaction between a sample with a first portion of an electromagnetic radiation. An associated sensor combines an interacted first portion of the electromagnetic radiation with a second portion of the electromagnetic radiation to produce a signal in a photo-detector. An analyzer determines changes in the signal and correlates the changes with a presence, absence, or a change in the characteristic in the sample. In that regard, the embodiments disclosed herein interferometrically combine the interacted first portion and the second portion of the electromagnetic radiation (e.g., as in a Mach-Zehnder type interferometer). Sensors of a type consistent with the present disclosure may include chemical sensors, pH sensors, biological sensors, and other environmentally sensitive devices such as physical sensors correlating an optical signal to a fluid density.

As used herein, the term "characteristic" refers to a chemical, mechanical, or physical property of a substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be detected with the sensors described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, combinations thereof, state of matter (solid, liquid, gas, emulsion, mixtures, etc.), and the like.

As used herein, the term "substance," "sample," "sample substance," or variations thereof, refers to at least a portion of matter or material of interest to be tested or otherwise evaluated using embodiments described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, de-foamers, breakers, scavengers, stabilizers, clarifiers, detergents, a treatment fluid, fracturing fluid, a formation fluid, or any oilfield fluid, chemical, or substance as found in the oil and gas industry.

As used herein, the term "electromagnetic radiation" includes radio waves, microwave radiation, terahertz, near/mid/deep infrared radiation, visible light, ultraviolet light, X-ray radiation and gamma ray radiation.

As used herein, the term "optically interact" or variations thereof refers to the reflection, transmission, scattering, diffraction, interference, or absorption of electromagnetic radiation either on, through, or from one or more processing elements, a substance being analyzed by the processing elements, or a polarizer. Accordingly, optically interacted light refers to electromagnetic radiation that has been reflected, transmitted, scattered, diffracted, interfered, or absorbed by, emitted, or re-radiated, for example, using a sensitized coating, but may also apply to optical interaction with a substance or a polarizer. In operation, a sensor as described herein is capable of distinguishing electromagnetic radiation related to a characteristic of interest of a substance from electromagnetic radiation related to other components of the substance.

Embodiments disclosed herein include sensors for measuring a characteristic of a sample substance by interacting electromagnetic radiation with the sample substance. Sensors based on interferometry show high sensitivity. An interferometer, in embodiments consistent with the present disclosure, splits coherent electromagnetic radiation into at least two portions that effectively travel different optical paths before being recombined and detected. An optical path length is defined as the product of the refractive index of the material the radiation or light is propagating through and the physical propagation distance or length. For waveguides, the effective refractive index used in the calculation of optical path length is based on the propagation velocity of waves in the waveguide. The difference in the optical path lengths between a first portion and a second portion of the electromagnetic radiation creates a change in interference fringe pattern upon recombination. The fringe pattern carries information regarding a sample property of interest (e.g., substance or analyte concentration among many others). The fringe pattern provides a sensitive measure of the phase shift induced by propagation of radiation under the presence (or absence) of an analyte of interest. Accordingly, interferometric techniques as disclosed herein allow for enhanced sensitivity at very low concentrations of the analyte of interest.

Embodiments as disclosed herein use interferometry with chemically sensitized optical waveguides to enhance detection sensitivity while maintaining device simplicity and compactness. In extreme environmental conditions, a waveguide structure embedded in a 3D substrate is well suited for interferometry. The oil and gas industry may benefit from such embodiments by using already deployed fiber optic cables and infrastructure in oil wells and pipelines. Embodiments as disclosed herein may be used in the inspection and maintenance of oil and gas pipelines used for long-haul transportation, or within refineries and storage facilities.

Embodiments in this disclosure combine existing technologies used in the manufacturing of optical fibers to form waveguides on interior and exterior surfaces of a 3D substrate. Pairs of waveguides are formed into Mach-Zehnder interferometers. A coating to selectively absorb, capture, bind, or otherwise immobilize a target analyte (i.e., characteristic) is applied to one arm of the Mach-Zehnder interferometer while the reference arm remains uncoated. In some embodiments, coherent light illuminates one end of the 3D substrate and launches light into both sensing and reference arms. Since one arm is coated and one is not, the quantity of the target analyte absorbed, captured, bound, or immobilized will cause a change in phase difference at the output of the two arms. Light leaving the two arms will spread out or diffract as it propagates through free space, overlapping and forming an interference pattern on an optical detector. The interference pattern observed at the detector, or a received irradiance of a single detection point is a function of the analyte absorbed, captured, bound, or immobilized in the coated arm.

Sensors as disclosed herein incorporate a plurality of waveguides into a 3D structure arranged in various configurations to detect one or more properties of a downhole environment. Sensitivity and specificity of sensors as disclosed herein are enhanced by coating alternating waveguide channels with a sensitized coating layer or film. The sensitized coating can be located on an outer surface or an inner surface of the 3D structure, depending on the configuration of the sensor. In either configuration, the sensitized coating is located on a surface exposed to the sample. Some embodiments include one or more different sensitized coatings to interact with one or more analytes of interest in the sample. In this sense, combinations for analyte detection are unlimited, as functional coatings are identified for different target analytes of interest. The interaction of an analyte with a sensitized coating causes a change in the refractive index of the coating. The change in the coating refractive index changes the propagation constant of the coated waveguide. Some embodiments use the interaction of an evanescent field from a propagating waveguide mode with the sensitized waveguide surface to change an interference pattern between the light emanating from the sensitized waveguide and light emanated from a reference waveguide. This change is generally proportional to analyte concentration.

A sensitized coating is activated when it absorbs, binds, attaches, or adheres to a target analyte(s) such that the refractive index of the sensitized coating changes. This changes the propagation constant of the sample waveguide, thereby giving rise to a phase shift of light (i.e., electromagnetic radiation) emerging from the sample waveguide. If an interferometer is constructed containing the sample waveguide and an uncoated reference waveguide, the output of the interferometer changes in response to activation of the sample waveguide by the presence of the target analyte. An analyzer determines a target analyte concentration based on the change in the interference pattern. Embodiments disclosed herein include arrangements of sample and reference waveguides to make an interferometry configuration simple to adapt for field applications and for simultaneous measurement of multiple target analytes.

In some embodiments, the plurality of waveguides forms an array having a circular cross-section relative to the light propagation in the waveguides. This configuration makes the sensor suitable for downhole and pipeline applications in the oil and gas industry. Embodiments consistent with this disclosure include small and robust chemical sensors that use relatively low power and are relatively inexpensive to fabricate. Furthermore, sensors according to this disclosure have the ability to measure a plurality of sample characteristics of interest simultaneously with no moving parts.

FIG. 1 illustrates an exemplary measurement system 101 including a sensor 100 incorporating waveguides 114 in a 3D substrate 105, according to some embodiments. In embodiments consistent with the present disclosure, sensor 100 may be a chemical sensor configured to detect the presence and/or concentration of one or more chemical analytes of interest in a sample. Sensor 100 includes a light source 102, and a beam splitter element 104 to separate the electromagnetic radiation emitted from the light source 102 into a first electromagnetic radiation 110s and a second electromagnetic radiation 110r. Beam splitter element 104 may be any type of phase-preserving beam splitter as known to those of ordinary skill in the art. For example, beam splitter element 104 may be a fiber beam splitter or a beam splitter prism. Light source 102 may be a lamp, an LED, a laser, an electromagnetic radiation emitter, or even solar light. Sensor 100 includes a detector 118 that provides a signal to analyzer 160. The coherence length of the electromagnetic radiation emitted by light source 102 is desirably as long as or longer than the maximum difference in optical path lengths splitter element 104 to detector 118. Analyzer 160 includes a processor circuit 161 and a memory circuit 162. Analyzer 160 may also be configured to control light source 102.

According to some embodiments, at least one of waveguides 114 includes a surface that is exposed to a fluid 150 in a container 170. In some embodiments container 170 is a closed container that houses fluid 150. Some embodiments include an open container 170 having an inlet and an outlet so that fluid 150 is circulating or otherwise in motion. In some embodiments, fluid 150 may include a mixture of oil, gas, water, and mud (i.e., drilling fluid) commonly found in downhole environments associated with an oil and gas platform in the oil and gas industry. In other embodiments, however, fluid 150 may include a blood sample, and fluid container 170 may be a vile, a test tube, or a blood vessel in a patient's body. Further according to some embodiments, fluid 150 may be a food product, such as milk or water, and container 170 may be a bottle or package. In some embodiments container 170 may be a pipeline, a tube, or a conduit. For example, container 170 may be an oil or gas pipeline, a water pipeline for agricultural irrigation or drainage, a blood vessel, or another tissue in the human body. Container 170 may also be a line or fluid passage in a downhole tool or downhole sensor, or a sensor located at the surface.

FIG. 2A illustrates a cross-sectional view of an exemplary sensor 200a incorporating waveguides in a 3D substrate 205a, according to some embodiments. Chemical sensor 200a includes sample waveguides 214s and reference waveguides 214r embedded in or otherwise positioned on substrate 205a. Waveguides 214s and 214r are collectively referred to hereinafter as waveguides 214. Sample waveguides 214s include a sensitized coating 212, 222, 232, and 242. Reference waveguides 214r are similar in all respects to sample waveguides 214, except for sensitized coatings 212, 222, 232, and 242. It is desirable that sensitized coatings 212, 222, 232, and 242 provide a linear, reversible, secure, and high target specificity.

In some embodiments, substrate 205a includes a preform, re-shaped using techniques well-known in the optical fiber industry. Accordingly, in some embodiments, 3D substrate 205a is a glass cylinder. It should be noted that the cross-section of the final 3D substrate 205a is a scaled down version of the preform. In embodiments where the preform is a solid rod-like structure, waveguides 214 could be located along the outer diameter (OD) of the rod. To efficiently propagate electromagnetic radiation, waveguides 214 are formed of a material having a higher refractive index ($n_1$) than the material in substrate 205a with refractive index ($n_2$, i.e., $n_2 < n_1$).

Sensing channels 210, 220, 230, and 240 are indicated by dashed lines. For each sensing channel 210, 220, 230, and 240, the signal portions of the electromagnetic radiation are injected into or otherwise conveyed through signal waveguides 214s, and the reference portions of the electromagnetic radiation are injected into or otherwise conveyed through reference waveguides 214r. Ideally, the coherent light illuminating for both reference and sensing waveguides should be in phase. For each sensing channel 210, 220, 230, and 240 an output electromagnetic radiation from waveguide 214s forms an interference pattern with an output electromagnetic radiation from waveguide 214r. An interference pattern for each of sensing channels 210, 220, 230, and 240 can be measured independently. Thus, sensor 200a can measure a plurality of analytes either simultaneously or overlapping in time. Waveguides 214s include sensitized coatings 212, 222, 232, and 242 on a side of the waveguide exposed to the outside or 3D substrate 205a. Each of sensitized coatings 212, 222, 232, and 242 may be selected to chemically interact with a target analyte.

FIG. 2B illustrates a cross-sectional view of a chemical sensor 200b incorporating waveguides 214 in a hollow or cylindrical 3D substrate 205b, according to some embodiments. Sensor 200b is similar to chemical sensor 200a, and operates under the same principles. In that regard, chemical sensor 200b differs from sensor 200a in that substrate 205b is a hollow, 3D structure. Furthermore, in sensor 200b waveguides 214 are disposed along the inner diameter (ID) of substrate 205b. Accordingly, fluid 150 is contained or flowing through a lumen or cavity 207 defined within hollow substrate 205b.

FIGS. 2A and 2B show the arrangement of waveguides 214 on an exposed surface of a 3D substrate to form sensing channels 210, 220, 230, and 240 as a plurality of interferometers arranged in a 3D configuration. More particularly, a 3D configuration in substrates 205a and 205b includes a cross-section and a length, where the length extends along a longitudinal axis of a wellbore in oil and gas exploration and extraction operations. In some embodiments, the exposed surface is in contact with fluid 150. More generally, the exposed surface is coupled to the substance containing an analyte of interest for measurement. The exposed surface may be external to an internal diameter of the 3D substrate (e.g., substrate 205a) or contained within the internal diameter of the 3D substrate (e.g., substrate 205b). In embodiments consistent with the present disclosure, the exposed surface may include a side surface of each waveguide 214, or at least one of waveguides 214. More generally, the exposed surface may include a side surface of at least one of waveguides 214, and a portion of the 3D substrate. Advantageously, the cylindrical geometry of sensors 200a and 200b matches the general symmetry of downhole and pipeline inspection tools in the oil and gas industry. More generally, the exposed surface of the 3D substrate may be curved in a direction perpendicular to a light propagation in waveguides 214 (i.e., the outer diameter in FIG. 2A and the inner diameter in FIG. 2B are perpendicular to waveguides 214). In some embodiments, the outer diameter (OD) of 3D substrates 205a and 205b is between about 1/16" and about ⅛". The cross-sectional dimension of waveguides 214 may be on the order of the size of the wavelength of light propagating through the waveguides. In that regard, waveguides 214 may be single mode or multimode waveguides, without limiting the embodiments disclosed herein.

While FIGS. 2A and 2B illustrate waveguides 214 having a somewhat square profile, the specific cross-sectional shape and size of waveguides 214 is not limiting. Rather, waveguides 214 may have any cross-sectional shape and size as desired for efficient electromagnetic radiation propagation and efficient fabrication. In that regard, the cross-sectional shape and size of each pair of waveguides 214s and 214r within each one of sensing channels 210, 220, 230, and 240 is similar or the same.

Sensitized coatings 212, 222, 232, and 242 may include hydrophobic or hydrophilic gels. Accordingly, either by swelling or shrinking, a change in the refractive index and the geometry of waveguides 214s induces a phase shift in the sample portion of radiation propagating therethrough. In some embodiments, the sensitized coating 212, 222, 232, and 242 is a porous material that is filled or emptied by the target analyte. A hydrophilic gel will shrink or swell in the presence of water or oil in fluid 150. Likewise, a hydrophobic gel may shrink or swell in the presence of water or oil in the fluid. Thus, a chemical sensor as disclosed herein may be used to measure water and oil content in a water/oil mixture.

In some embodiments, sensitized coatings 212, 222, 232, and 242 target gaseous hydrocarbons ranging from methane to hexane, and other hydrocarbons and related chemical species of relevance to the oil and gas industry. In such embodiments, sensitized coatings 212, 222, 232, and 242 may include a thin polymer layer related to the selected hydrocarbon. Moreover, in some embodiments coatings 212, 222, 232, and 242 may include embedded nanoparticles to enhance target specificity, such as metal nanoclusters, quantum dots, and plasmon resonant schemes. Other embodiments include coatings 212, 222, 232, and 242 having ion sensitivity for applications such as pH sensors.

Analytes or characteristics that may be of relevance for targeting with sensors as disclosed herein include Iron ions or Alkaline metals dissolved in fluid 150. In some embodiments, it is desirable to measure gaseous concentrations in fluid 150, such as $CO_2$ or Methane ($CH_4$). More generally, sensors consistent with embodiments disclosed herein may include pollutants, agrochemicals, nerve agents, explosives, pharmaceuticals, and controlled substances (e.g., illegal drugs).

Accordingly, sensors as disclosed herein may have multiple applications depending on the target analyte in fluid 150. For example, applications for measuring bacteria contamination in fluid 150 include specific bacterial antibodies in sensitized coatings 212, 222, 232, and 242. Moreover, in some embodiments a sensor as disclosed herein includes at least one of coatings 212, 222, 232, and 242 sensitized with an antibody having affinity to certain types of cancer cells, or to a carcinoembryonic antigen (CEA). More generally, sensitized coatings 212, 222, 232, and 242 may target pathogens associated with a disease such as a bacterium, a unicellular microorganism, a strand of nucleic acid (e.g., DNA or RNA), a protein or a peptide. Other examples of target pathogens for sensitized coatings 212, 222, 232, and 242 include, but are not limited to, Bacillus anthracis (Anthrax), Mycobacterium tuberculosis lipoarabinomannan (LAM), Vibrio cholerae, Escherichia Coli (E. Coli), or the Influenza virus. Other biological agents targeted by sensitized coatings 212, 222, 232, and 242 include spores, toxins, viruses, and water borne pathogens. Accordingly, coatings 212, 222, 232, and 242 may include covalently bonding an antibody or antigen on the exposed surface of waveguides 214. Thus, sensors as disclosed herein are configured to determine a unicellular microorganism presence in a sample, or a unicellular microorganism concentration in the sample.

Other examples for the use of sensors as disclosed herein include DNA sensors having short, single-stranded (desoxyribonucleicacid) DNA oligonucleotides grown on the surface of a quartz or silica waveguide 214. Sensitized coatings 212, 222, 232, and 242 for use in biological sensing may include material layers such as silane-based self-assembled monolayers. Accordingly, silane-based monolayers may be sensitized by amine radical termination including a mixture of carboxylic acid-terminated polyethylene glycol (PEG) chains.

In fluid 150, sensitized coatings 212, 222, 232, and 242 may reach equilibrium with a target analyte concentration after a given response time. It is desirable that the equilibrium be reached below a saturation point for a plurality of ligands included in sensitized coatings 212, 222, 232, and 242. In that regard, when target analyte concentration increases, it may be desirable that the coating response increases at a first rate. When target analyte concentration decreases, it is desirable that the coating response decreases at an equivalent second rate. Accordingly, it is desirable that sensitized coatings 212, 222, 232, and 242 have a reversible and linear response to target analyte concentration. Thus, it is desirable that sensitized coatings 212, 222, 232, and 242 reach an equilibrium point that is proportional to analyte concentration in fluid 150. Response times and saturation points vary substantially from one type of sensitized coating to another. In general, it is desirable that sensitized coating 212, 222, 232, and 242 have a fast, linear, and reversible response.

In order to correct for aging and degradation effects in sensitized coatings 212, 222, 232, and 242, some embodiments include periodic calibration procedures on sensors 200a and 200b. Furthermore, some embodiments include a heater to drive back the sensitized coating to a baseline (or unsaturated) value. Some embodiments include calibration measurements to determine sensor replacement or when to refresh or clean the sensitized coating.

Figures 3A, 3B:
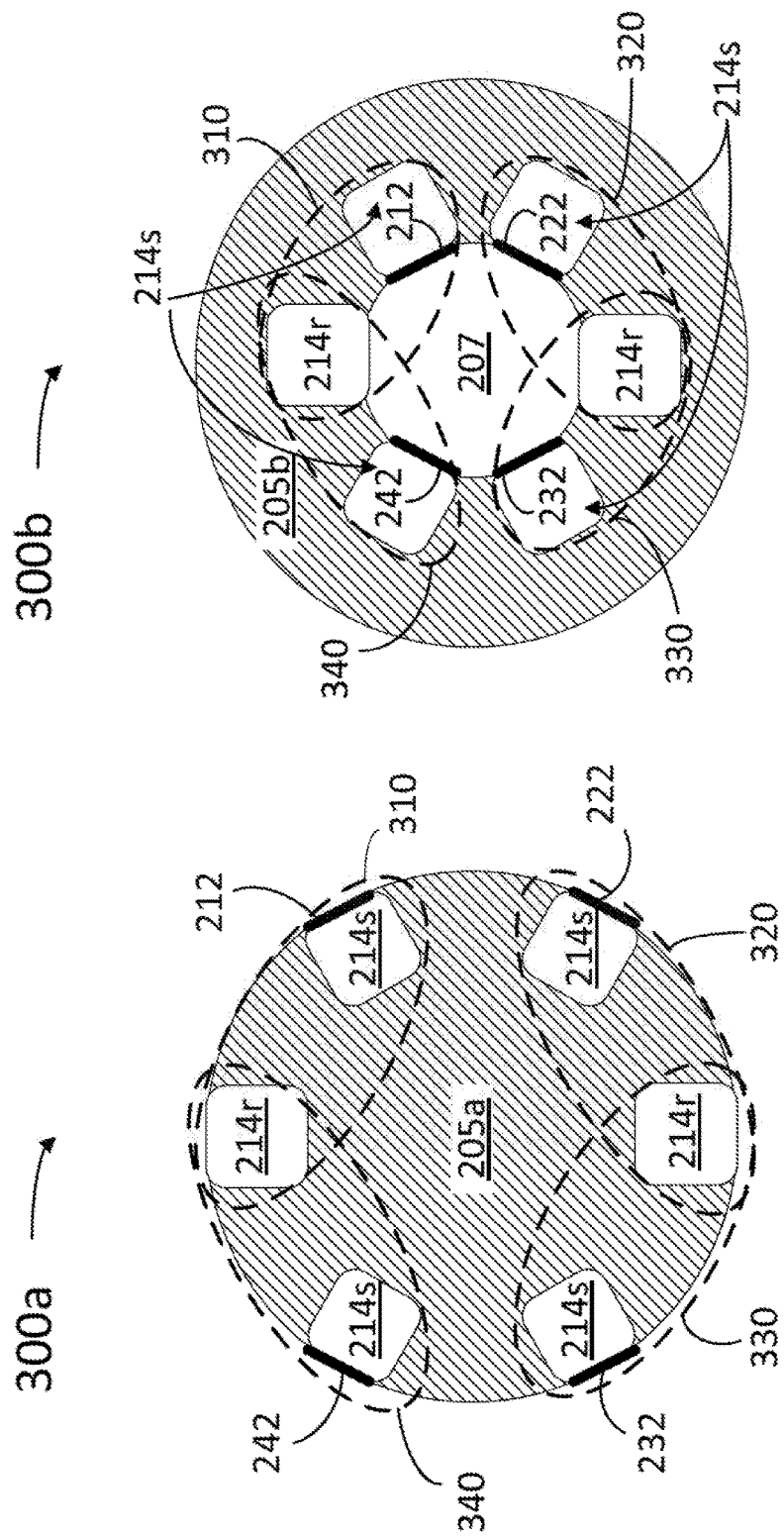
FIG. 3A illustrates a cross-sectional view of a sensor incorporating waveguides in a 3D substrate, according to some embodiments.
FIG. 3B illustrates a cross-sectional view of a sensor incorporating waveguides in a 3D substrate, according to some embodiments.

FIG. 3A illustrates a cross-sectional view of an exemplary sensor 300a incorporating waveguides 214 in 3D substrate 205a, according to some embodiments. Sensor 300a is similar to sensor 200a, described in detail above (cf. FIG. 2A). Sensor 300a includes sensing channels 310, 320, 330 and 340. Sensing channel 310 includes sensitized coating 212, and therefore has a similar function as sensing channel 210 in sensor 200a. Likewise, sensing channel 320 includes sensitized coating 222, and therefore has a similar function as sensing channel 220 in sensor 200a. Sensing channel 330 includes sensitized coating 232, and therefore has a similar function as sensing channel 230 in sensor 100a. Moreover, sensing channel 340 includes sensitized coating 242, and therefore has a similar function as sensing channel 240 in sensor 200a.

As illustrated, sensing channels 310 and 340 share a first reference waveguide 214r, and sensing channels 320 and 330 share a second reference waveguide 214r. Thus, sensor 300a makes an efficient use of the total number of waveguides 214 embedded in 3D substrate 205a. Accordingly, sensor 300a increases the possible number of analytes detected simultaneously by reducing the total number of reference waveguides 214r.

FIG. 3B illustrates a cross-sectional view of a chemical sensor 300b incorporating waveguides 214 in hollow 3D substrate 205b, according to some embodiments. Sensing channels 310, 320, 330, and 340 in FIG. 3B are as described in detail above in reference to FIG. 3A. Substrate 205b is as described in FIG. 2B above.

More generally, embodiments consistent with the present disclosure use a single reference waveguide with multiple sample waveguides for detection of multiple analytes of interest. Furthermore, multiple analyte detection may be performed simultaneously or overlapping in time.

Figure 4:
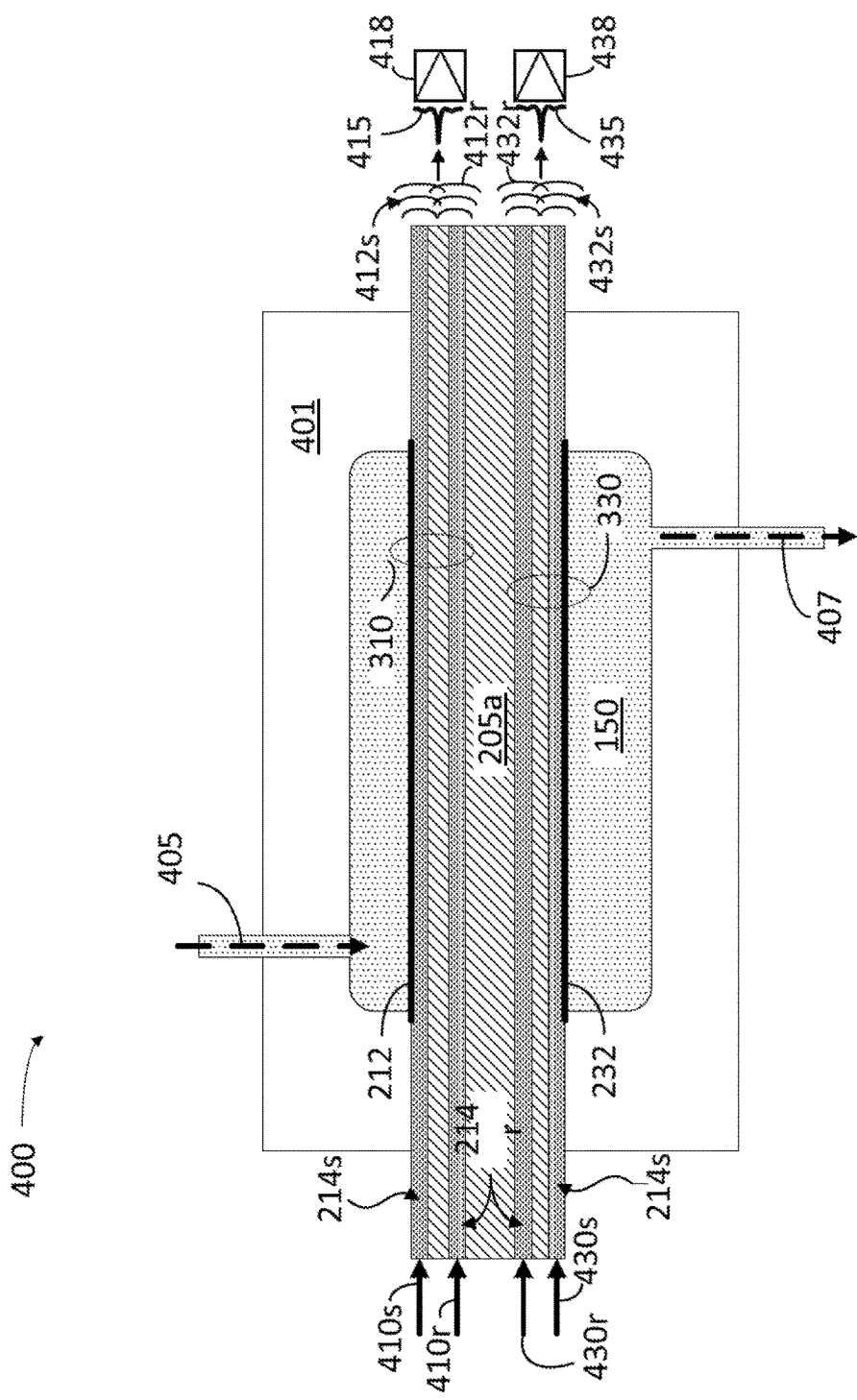
FIG. 4 illustrates a chemical sensor incorporating waveguides in an exterior surface of a 3D substrate, according to some embodiments.

FIG. 4 illustrates a chemical sensor 400 incorporating waveguides 214 (shown as waveguides 214r and 214s) in an exterior surface of 3D substrate 205a, according to some embodiments. Sensor 400 includes 3D substrate 205a inserted into a housing 401 containing fluid 150 flowing past sensor 400 from a fluid inlet 405 to a fluid outlet 407. Coherent light illuminates an input side of 3D substrate 205a and detectors 418 and 438 positioned at an output side of 3D substrate 205a read the individual interferometers formed by signal channels 310 and 330. While not limiting, some embodiments of sensor 400 include a 3D substrate 205a of about 1" to 2" in length.

A signal electromagnetic radiation 410s is coupled or otherwise conveyed into waveguide 214s and interacts with sensitized coating 212. As a result, a sample output signal 412s emerges from waveguide 214s. A reference electromagnetic radiation 410r is coupled or otherwise conveyed into waveguide 214r to form a reference output signal 412r. Sample output signal 412s optically interacts with reference output signal 412r to form interference pattern 415. Detector 418 measures a property of interference pattern 415. The distance between detector 418 and the end of waveguides 214 is selected to capture a specific portion of interference pattern 415. In some embodiments, detector 418 may be placed in the near field (about a few wavelengths away from the end of waveguides 214), to have greater sensitivity to changes in interference pattern 415. Further, in some embodiments, detector 418 may be placed with a sensitive area overlapping a peak in interference pattern 415. Some embodiments may include detector 418 with a sensitive area overlapping a dark node of interference pattern 415. Moreover, in some embodiments a sensitive area of detector 418 may overlap a transition region in interference pattern 415, the transition region including a portion of a peak and a portion of a dark node. In yet other embodiments, detector 418 may include a sensor array including a linear array of optical fibers, each optical fiber connected to a remote photo detector. In such a configuration, waveguides 214 may also be remotely illuminated and interrogated via fiber (e.g., from the surface in downhole applications); thus, sources and detectors can be located remotely, according to some embodiments. For downhole applications, this means at the surface, away from the harsh downhole environment that is not amenable to light sources and detectors.

In a similar manner, a first electromagnetic radiation 430s, and a second electromagnetic radiation 430r are coupled or otherwise conveyed into waveguides 214s and 214r, respectively. A sample output signal 432s is the result of interaction between first electromagnetic radiation 430s and sensitized coating 232. Accordingly, sample output signal 432s interacts with reference output signal 432r to form interference pattern 435. Detector 438 measures a property of interference pattern 435.

In one or more embodiments, electromagnetic radiation 410s, 410r, 430s, and 430r is part of a collimated, coherent beam of light illuminating the left hand side of the structure. Some embodiments may include electromagnetic radiation 410s coherent with electromagnetic radiation 410r as part of a focusing beam. Other configurations of electromagnetic radiation 410s and electromagnetic radiation 410r may include non-collimated beams. Accordingly, interference patterns 415 and 435 may be formed as sample output signal 412s and reference output signal 412r each propagate through free space.

In some embodiments, an optical element (not shown) may be placed between the output side of waveguides 214 and detector 418. For example, in some embodiments a micro-lens array may be placed between waveguides 214 and detector 418 to more efficiently direct interference pattern 415 to the sensitive area in detector 418. Detector 418 may be a single receiver to determine the brightness or irradiance of a central interference fringe in pattern 415 in configuration where the central fringe is approximately Gaussian in shape. Accordingly, pattern 415 moves up and down with respect to detector 418 in FIG. 4 in response to phase differences between sample output signal 412s and reference output signal 412r exiting waveguides 214s and 214r, respectively. Alternately, detector 418 may include an array of sensors used to better determine the position of the central fringe and secondary interferences in pattern 415, which may be also be analyzed to determine the phase difference. Detector 418 may include a lens to focus the central area of interference pattern 415 onto an optical fiber, or a plurality of optical fibers. Accordingly, light forming interference pattern 415 can be transmitted to a remote photodiode sensor via the optical fiber, or the plurality of optical fibers receiving at least a portion of interference pattern 415 at a selected location.

In embodiments consistent with the present disclosure, detectors 418 and 438 may include a plurality of sensitive areas in a detector array. Thus, detectors 418 and 438 may collect a portion of interference patterns 415 and 435, respectively, and perform a detailed analysis or computation. In embodiments consistent with the present disclosure, detectors 418 and 438 may be included in a detector array. In some embodiments, the entire body of sensor 400 may be immersed in fluid 150 to perform simultaneous or time overlapped measurements of multiple analytes. In yet other embodiments, only a portion of the OD in substrate 205a may be exposed to the fluid (e.g., the portion exposing sensing channel 210) at a given moment. In such a configuration, sensor 400 may incorporate a rotating mechanism to rotate substrate 205a about its longitudinal axis to perform a second measurement (e.g., rotating substrate 205a to expose sensing channel 220). Accordingly, in some embodiments housing 401 maintains detectors 415 and 435 in a desired position relative to 3D substrate 205a. In some embodiments, substrate 205a moves longitudinally inside housing 401 so that a fresh portion of coatings 212 and 232 is exposed to fluid 150.

Figure 5:
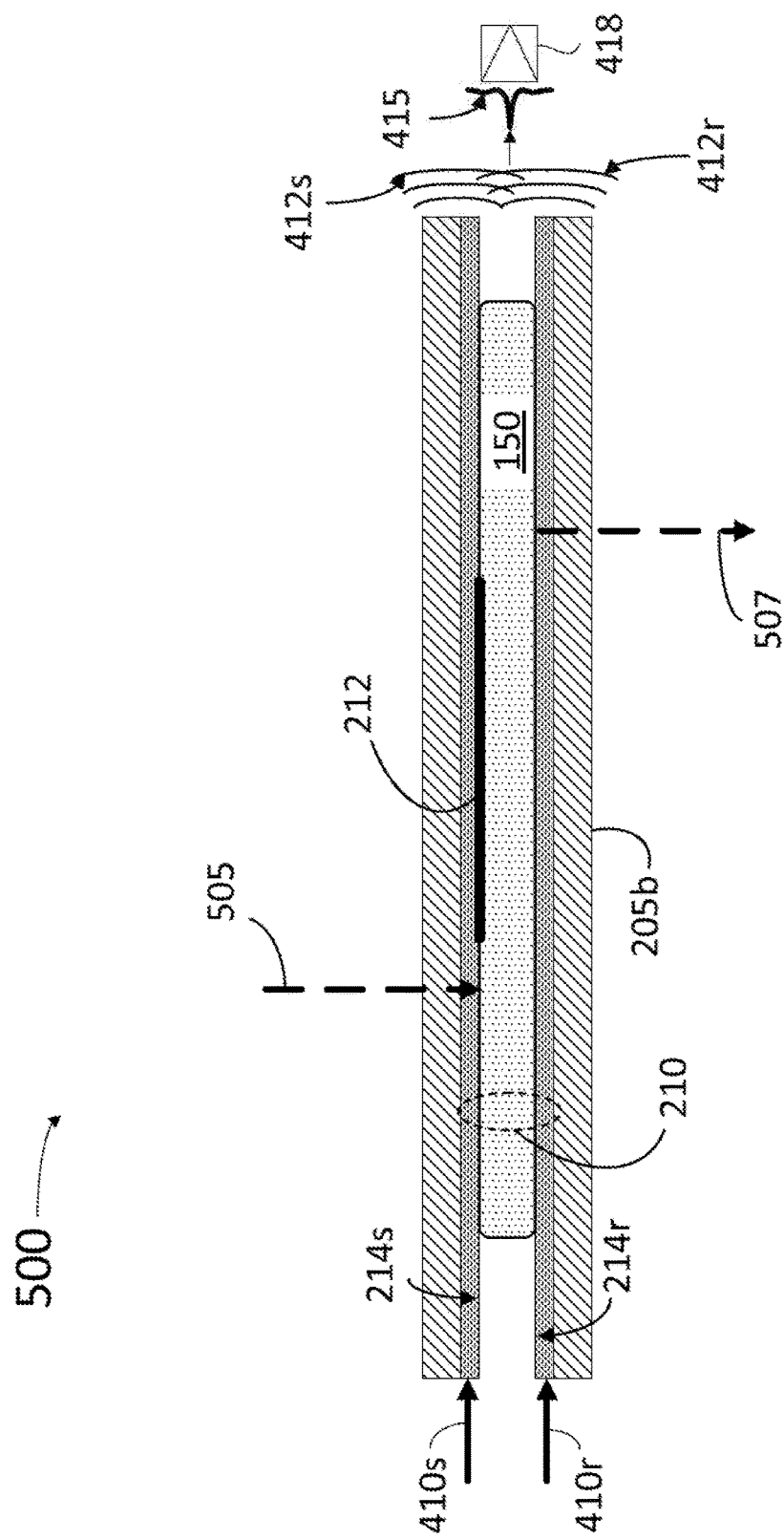
FIG. 5 illustrates a chemical sensor incorporating waveguides in an interior surface of a 3D substrate, according to some embodiments.

FIG. 5 illustrates a sensor 500 incorporating waveguides 214 in an interior surface of a 3D substrate 205b, according to some embodiments. In FIG. 5, fluid 150 flows from an inlet 505 to outlet 507 through a portion within an inner diameter of substrate 205b. FIG. 5 depicts one sensing channel 210 for illustration purposes only. A plurality of sensing channels may be included, consistent with embodiments disclosed herein (e.g., channels 210, 220, 230, 240, cf. FIG. 2B, or channels 310, 320, 330, and 340, cf. FIG. 3B).

FIGS. 4 and 5 illustrate a Mach-Zehnder configuration where a beam splitter is replaced by illuminating waveguides 214s and 214r with coherent, collimated light. Another advantageous feature in some embodiments of chemical sensors 400 and 500 is that output light 412s and 412r is combined in free space propagation into interference pattern 415 as in a "two slit" interference pattern. Accordingly, embodiments of chemical sensors consistent with FIGS. 4 and 5 are compact, simpler and cheaper to fabricate than existing interferometric waveguide based chemical sensors.

Figure 6B:
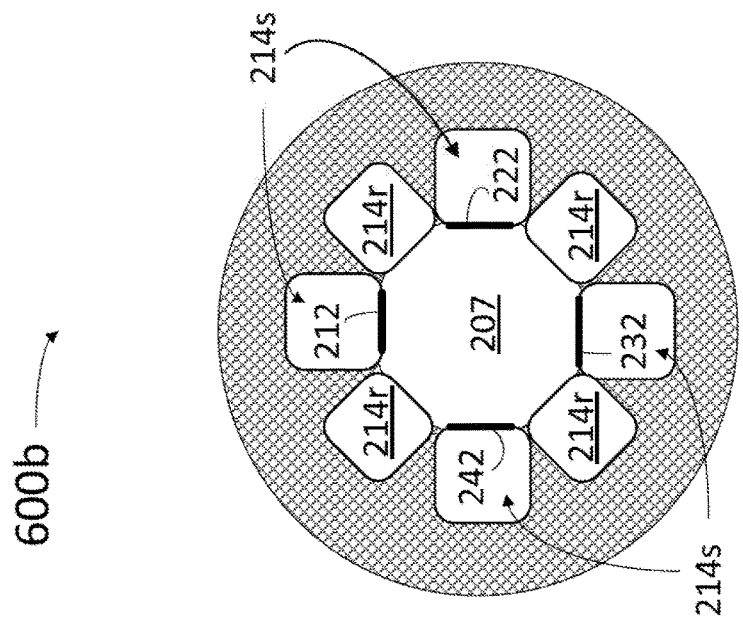
FIG. 6B illustrates a cross-sectional view of a sensor incorporating waveguides in an interior surface of a 3D substrate, according to some embodiments.
Figure 6A:
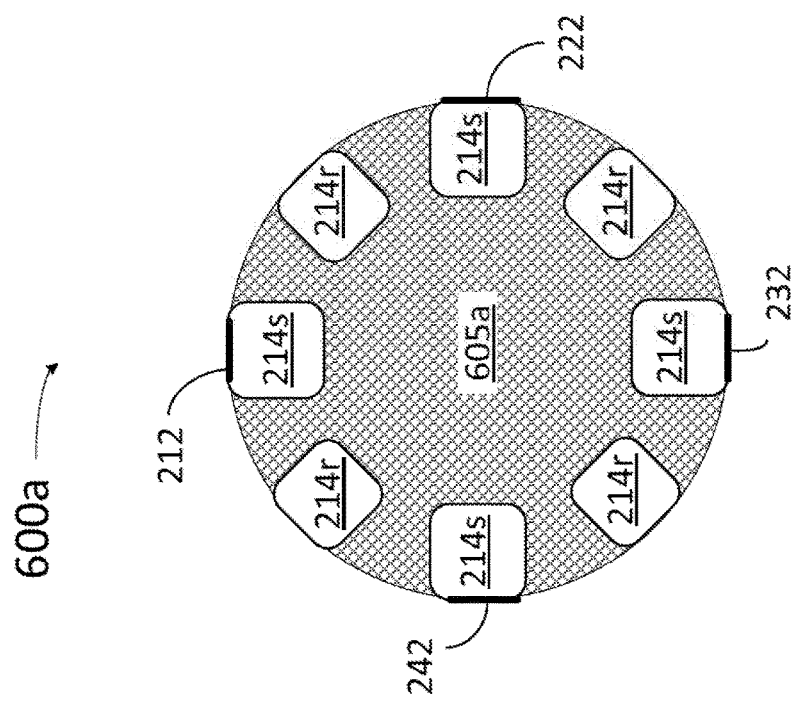
FIG. 6A illustrates a cross-sectional view of a sensor incorporating waveguides in an exterior surface of a 3D substrate, according to some embodiments.

FIG. 6A illustrates a cross-sectional view of a chemical sensor 600a incorporating waveguides 214 in an exterior surface of a 3D substrate 205a, according to some embodiments. A mask 605a in sensor 600a overlaps transparent portions that are not waveguides 214 on the side of sensor 600a including the optical output of waveguides 214. Mask 605a improves the signal-to-noise ratio (SNR) from the output of waveguides 214.

FIG. 6B illustrates a cross-sectional view of a chemical sensor 600b incorporating waveguides 214 in an interior surface of a 3D substrate, according to some embodiments. A mask 605b (best seen in FIG. 6C) included in sensor 600b overlaps the end of the sensor tube, serving a similar purpose as mask 605a in sensor 600a, above (cf. FIG. 6A).

Masks 605a and 605b block background electromagnetic radiation that may propagate through the bulk of 3D substrates 205a and 205b and may confuse the interference pattern formed at the detectors (e.g., interference patterns 415 and 435, cf. FIG. 4). In that regard, masks 605a and 605b may be formed of a material that is opaque or substantially opaque to the electromagnetic radiation propagating through waveguides 214. Masks 605a and 605b limit the illumination from light source 102 mostly to waveguides 214. Accordingly, masks 605a and 605b avoid illumination of the entire 3D structure, which is glass in some embodiments. In some embodiments, the portion of the cross section of the 3D structure occupied by waveguides 214 is small in comparison to the entire cross section of the 3D structure. Accordingly, masks 605a and 605b increase the optical interferometric signal over a background optical signal, thus facilitating phase difference detection between waveguides 214r and 214s.

FIG. 6C illustrates a side view of sensor 600a of FIG. 6A and sensor 600b of FIG. 6B, according to some embodiments. As shown in FIG. 6C, mask 605a is disposed on a surface of substrate 205a facing detectors 418 and 438 (cf. FIG. 4). Likewise, mask 605b is disposed on a surface of substrate 205b facing detector 418 (cf. FIG. 5).

Figure 7:
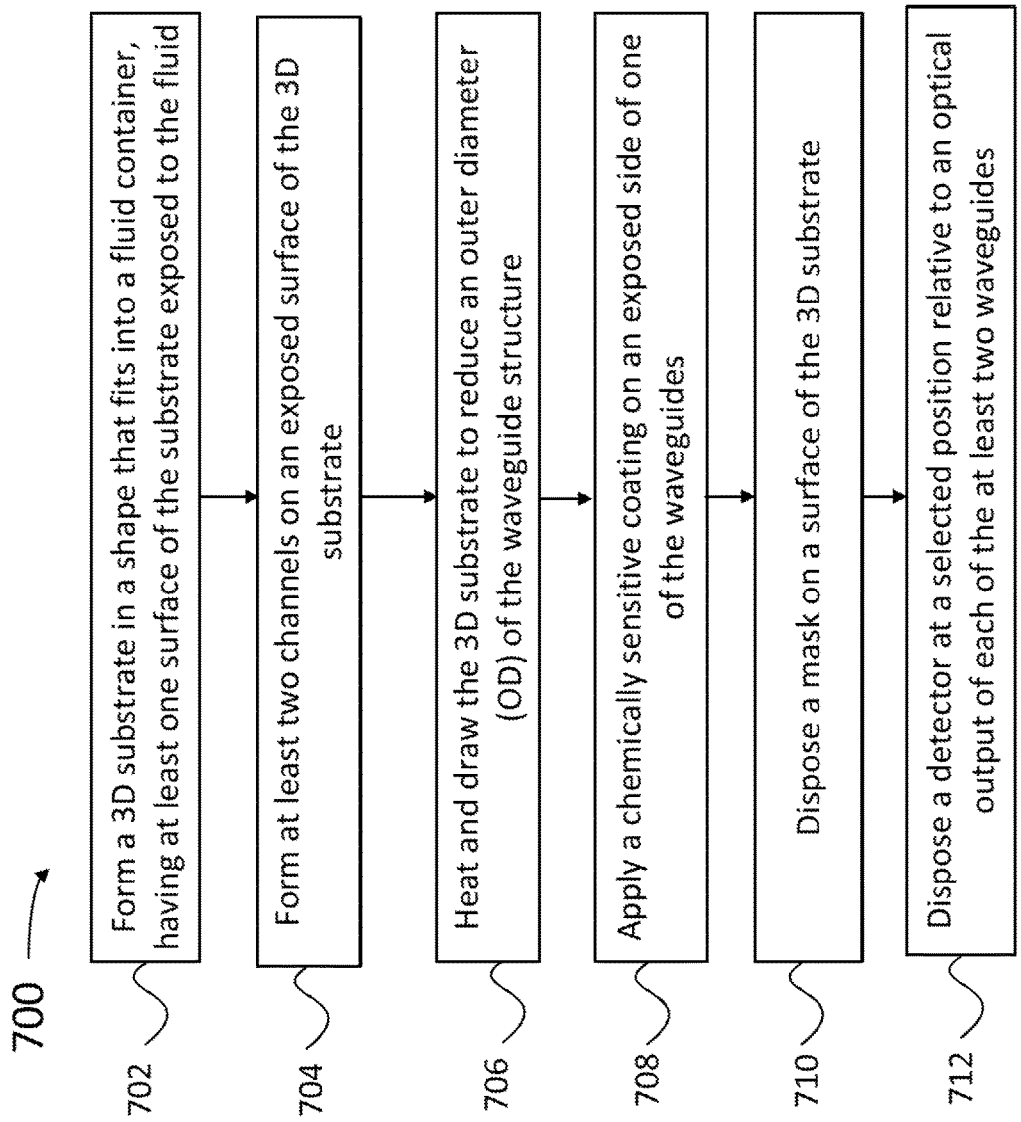
FIG. 7 illustrates a flow chart including steps in a method for fabricating a sensor incorporating waveguides in a 3D substrate, according to some embodiments.

FIG. 7 illustrates a flow chart including steps in a method 700 for fabricating a sensor incorporating waveguides in a 3D substrate, according to some embodiments. The sensor in method 700 may include a 3D substrate having a cross-section and a length, the substrate supporting a plurality of waveguides embedded in the substrate (e.g., waveguides 214 in sensors 100a, 100b, 300a, and 300b, cf. FIGS. 2A, 2B, 3A, and 3B, respectively). The substrate may further include an exposed surface having at least a portion of a side surface of each waveguide, and sensitized coatings in the portion of the side surface of at least one of the plurality of waveguides (e.g., sensitized coatings 212, 222, 232, and 242). Methods consistent with the present disclosure may include at least one of the steps in method 700, and not others. Likewise, methods consistent with method 700 may include all the steps in method 700, in addition to other steps. Moreover, the specific order of the steps illustrated in FIG. 7 is not limiting of different embodiments consistent with method 700. In that regard, methods consistent with method 700 may include steps as illustrated in FIG. 7 performed in different order, or at least two or more steps overlapping in time, or even two or more steps performed simultaneously.

Step 702 includes forming the 3D substrate in a shape that fits into a fluid container, such that the 3D substrate may have at least one surface exposed to the fluid. Accordingly, in some embodiments step 702 may include using a preform in the shape of a solid or hollow rod structure. Step 702 may also include selecting a material having a given index of refraction for the preform (e.g., $n_2$). Step 702 should also include forming longitudinal regions with a higher refractive index than the bulk regions. The regions with higher refractive index will form the waveguides, after drawing the preform down to its final size. For example, step 702 may include selecting a 3D structure made of glass. Step 704 includes forming at least two channels on an exposed surface of the 3D substrate. The at least two channels in step 704 will become waveguides once the preform is formed into a waveguide structure, when the preform is drawn to its final size. Accordingly, step 704 may include selectively increasing the index of refraction of the selected portions of the preform (i.e., the at least two channels) to a value $n_1$ ($n_2 < n_1$). In some embodiments, step 706 includes doping portions of the glass preform with heavy ions, or illuminating portions of the glass preform with electromagnetic radiation (such as ultra-violet radiation, or X-ray radiation). A preform as used in steps 702 through 704 may be on the order of ½ to 3 inches in diameter, according to some embodiments. Step 704 may include depositing, growing, fusing, inserting, or otherwise embedding channels with higher refractive index than the majority of the preform, in the preform. Step 706 includes heating and drawing the 3D substrate to reduce an outer diameter (OD) of the waveguide structure. Furthermore, step 706 may include heating and pulling the modified preform to a desired length in a draw tower.

Step 708 includes applying a sensitive coating on an exposed side of one of the waveguides. Accordingly, step 708 may include depositing a chemically sensitive coating using a chemical vapor deposition (CVD) technique. Other techniques for thin layer deposition as used in the semiconductor and biomedical industries may be included and otherwise employed in step 708. Step 710 includes disposing a mask on surfaces of the 3D substrate. Accordingly, in some embodiments step 710 includes disposing the mask on a surface that will face the detector. Furthermore, in some embodiments step 710 includes disposing a mask also in a surface of the 3D substrate facing the source of collimated light. In that regard, step 710 enhances removal of an optical background from a signal measured by the detector.

Step 712 includes disposing a detector at a selected position relative to an optical output of each of the at least two waveguides. Accordingly, step 712 may include disposing the detector so that the sensitive area of the detector overlaps a peak, or a dark node in an interference pattern formed by the waveguides embedded in the 3D substrate. Moreover, step 712 may include disposing the detector so that the sensitive area of the detector overlaps a portion of a peak and a portion of a dark node in the interference pattern. Step 712 may further include disposing the 3D substrate including the waveguides, and the detector, in a housing that protects the chemically sensitive coating and maintains the detector in the desired position.

Figure 8:
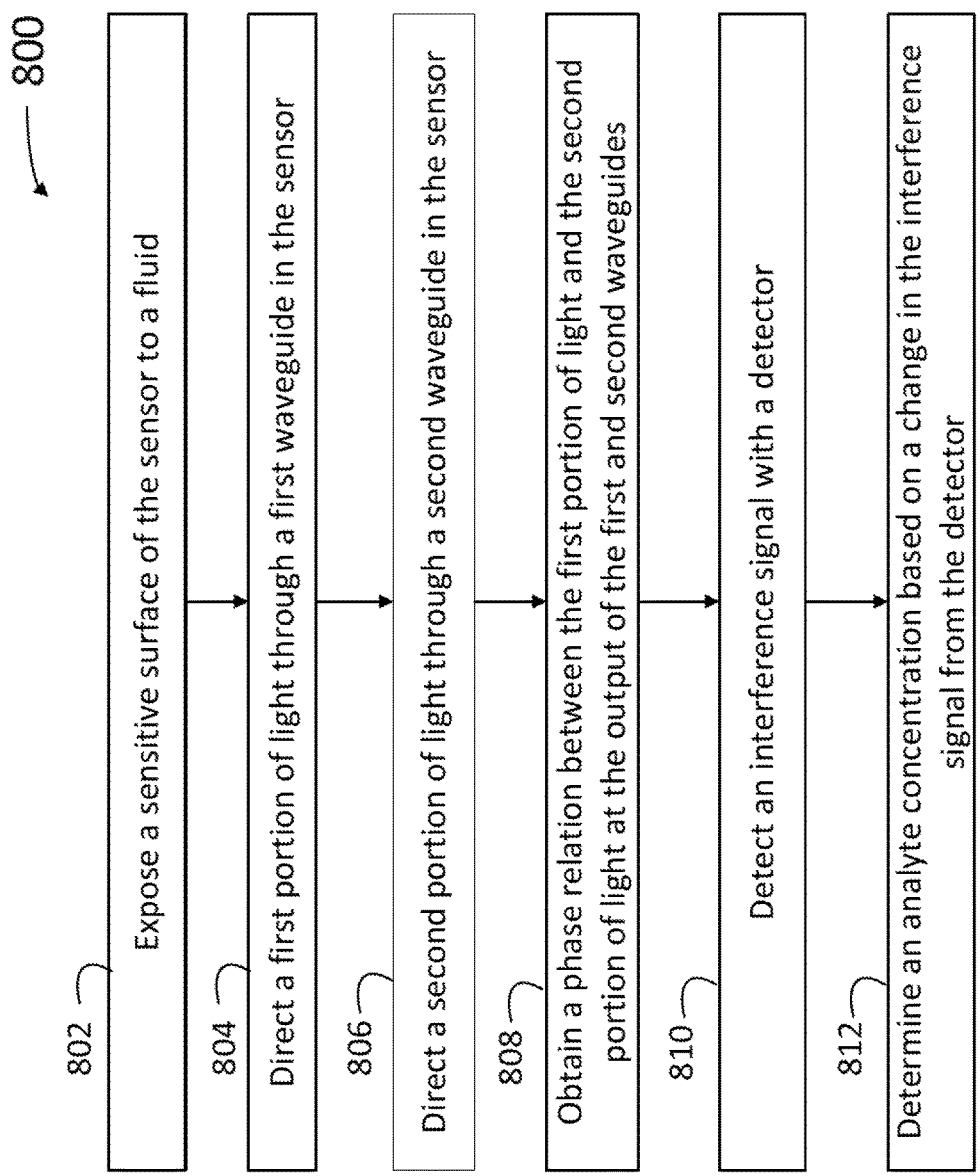
FIG. 8 illustrates a flow chart including steps in a method for measuring a characteristic of a sample using a sensor, according to some embodiments.

FIG. 8 illustrates a flow chart including steps in a method 800 for measuring a characteristic of a sample using a sensor, according to some embodiments. Method 800 may include using a light source, a beam-splitter, a sensor, and a detector in an interferometer configuration (e.g., light source 102, beam-splitter 104, sensor 100, and detector 118, cf. FIG. 1). Alternatively, the input beam splitter may be omitted by illuminating both waveguides of a sensing interferometer by a single, collimated, coherent beam that overlaps the two waveguides. The sensor may include a substrate having a cross-section and a length, the substrate supporting a plurality of waveguides embedded in the substrate (e.g., substrates 205a and 205b, and waveguides 214, cf. FIGS. 4 and 5). An exposed surface of the substrate includes least a portion of a side surface of each of the plurality of waveguides. The plurality of waveguides includes at least a sensing channel having a sample waveguide and a reference waveguide (e.g., sensing channels 210, 220, 230, and 240, cf. FIGS. 2A, B). Accordingly, the sample waveguide may include a sensitized coating in a side surface that is included in the exposed surface of the substrate (e.g., sensitized coatings 212, 222, 232, and 242, cf. FIGS. 2A, B). Moreover, method 800 may be performed by an analyzer including a processor circuit executing commands stored in a memory circuit (e.g., analyzer 160, processor circuit 161, and memory circuit 162).

Methods consistent with the present disclosure may include at least one of the steps in method 800, and not others. Likewise, methods consistent with method 800 may include all the steps in method 800, in addition to other steps. Moreover, the specific order of the steps illustrated in FIG. 8 is not limiting of different embodiments consistent with method 800. In that regard, methods consistent with method 800 may include steps as illustrated in FIG. 8 performed in different order, or at least two or more steps overlapping in time, or even two or more steps performed simultaneously.

Step 802 includes exposing a sensitive surface of the sensor to a fluid. In some embodiments, step 802 includes allowing a target analyte to reach equilibrium on the sensitive surface of the sensor. Step 804 includes directing a first portion of light through a first waveguide in the sensor. In some embodiments, step 804 may further include splitting a coherent light beam using a beam splitter element and selecting the first portion of light from a first port in the beam splitter. Step 806 includes directing a second portion of light through a second waveguide in the sensor. Accordingly, step 806 may include selecting the second portion of light from a second port in the beam splitter. In some embodiments, steps 804 and 806 take place simultaneously.

Step 808 includes obtaining a phase relation between the first portion of light and the second portion of light at the output of the first and second waveguides. Accordingly, step 808 may include placing a phase retardation element in the optical path length of the first portion of light or the second portion of light between the light source and at least one of the first and second waveguides. In some embodiments, step 808 may include selecting a light beam having a coherence length longer than a length of the waveguides in the sensor. In some embodiments, step 808 includes splitting a light beam from a light source into the first portion of light and the second portion of light with a phase-preserving beam splitter element. Accordingly, step 808 includes obtaining a phase difference that results from the different phase velocities (i.e. optical path lengths) between a sensitized waveguide and a reference waveguide, as disclosed herein.

Step 810 includes detecting an interference signal with the detector. In some embodiments, step 810 includes detecting a portion of the interference signal comprising at least one of a peak, a dark node, or a portion of a peak and a dark node. In some embodiments, step 810 may include determining an interference pattern using an array of sensitive areas in the detector, or an array of detectors. Accordingly, step 810 may include detecting an interference pattern with a two-dimensional detector array. Furthermore, in some embodiments step 810 includes detecting an interference pattern with a one-dimensional detector array. And step 812 includes determining the characteristic of the sample based on a change in the interference signal from the detector. In some embodiments, step 812 includes determining an analyte concentration based on a change in the interference signal from the detector. Accordingly, step 812 may include finding the characteristic of the sample in a lookup table having a list of characteristics of the sample and a list of changes in interference signal values.

Figure 9:
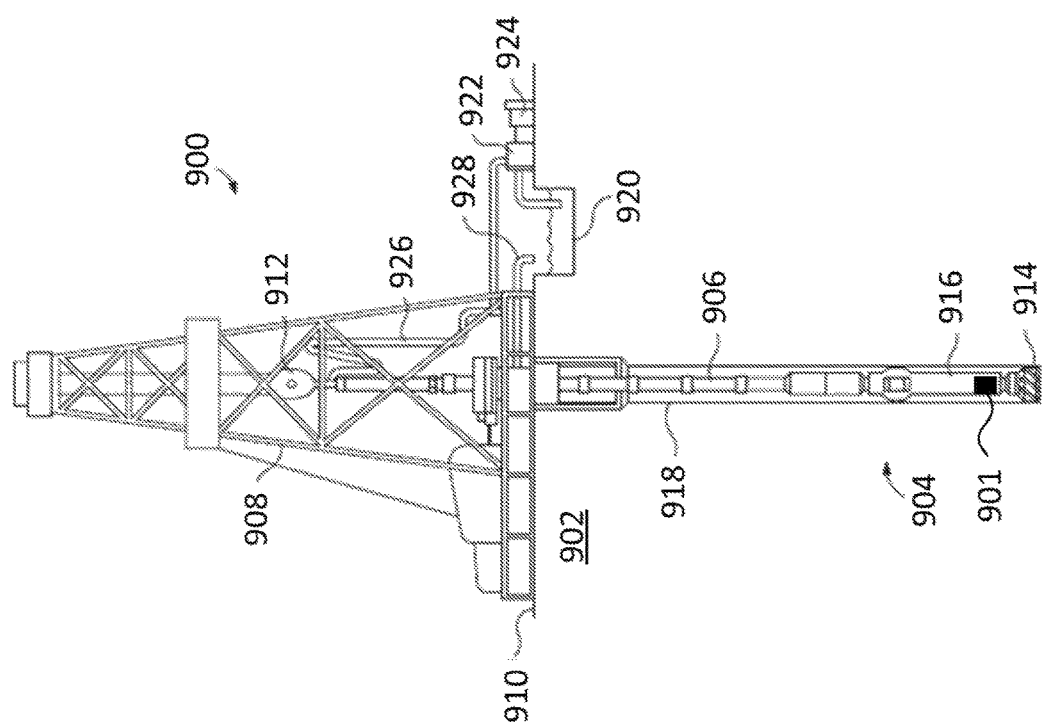
FIG. 9 illustrates an exemplary drilling system employing a sensor incorporating waveguides in a 3D substrate, according to some embodiments.

FIG. 9 illustrates an exemplary drilling system 900 employing a sensor 901 incorporating waveguides in a 3D substrate, according to some embodiments. Sensor 901 may be the same as or similar to any one of sensors 100, 200a, 200b described in detail in FIG. 1 and in FIGS. 2A-2B above. Boreholes may be created by drilling into the earth 902 using drilling system 900. Drilling system 900 may be configured to drive a bottom hole assembly (BHA) 904 positioned or otherwise arranged at the bottom of a drill string 906 extended into the earth 902 from a derrick 908 arranged at the surface 910. The derrick 908 includes a kelly 912 used to lower and raise the drill string 906.

The BHA 904 may include a drill bit 914 operatively coupled to a tool string 916 which may be moved axially within a drilled wellbore 918 as attached to the drill string 906. During operation, drill bit 914 penetrates the earth 902 to form wellbore 918. BHA 904 provides directional control of drill bit 914 as it advances into the earth 902. Tool string 916 can be semi-permanently mounted with various measurement tools such as a measurement-while-drilling (MWD) tool and a logging-while-drilling (LWD) tool, and sensor 901 may form part of one of the MWD or LWD tools to obtain downhole measurements of drilling conditions. In other embodiments, the measurement tools may be self-contained within the tool string 916, as shown in FIG. 9. In some embodiments, tool string 916 may include a fiber optic cable coupling a light source at surface 910 to sensor 901 (e.g., light source 102, cf. FIG. 1). The fiber optic cable may be configured to convey electromagnetic radiation to sensor 901 (e.g., electromagnetic radiation 110s and electromagnetic radiation 110r, cf. FIG. 1).

Fluid or "mud" from a mud tank 920 may be pumped downhole using a mud pump 922 powered by an adjacent power source, such as a prime mover or motor 924. The mud may be pumped from the mud tank 920, through a stand pipe 926, which feeds the mud into the drill string 106 and conveys the same to the drill bit 914. The mud exits one or more nozzles arranged in the drill bit 914 and in the process cools the drill bit 914. After exiting the drill bit 914, the mud circulates back to the surface 910 via the annulus defined between the wellbore 918 and the drill string 906, and in the process returns drill cuttings and debris to the surface. The cuttings and mud mixture are passed through a flow line 928 and are processed such that a cleaned mud is returned down hole through the stand pipe 926 once again. Sensor 901 may be configured to measure characteristics of the mud near where drill bit 914 forms wellbore 918. In that regard, mud in the wellbore near drill bit 914 may be the fluid to which sensor 901 is exposed, for measurement (e.g., fluid 150, cf. FIGS. 1, 4 and 5). In that regard, measurement procedures using sensor 901 may include any one or all of the steps in a method for measuring a characteristic of a sample using a sensor as disclosed herein (e.g., method 800, cf. FIG. 8).

Although drilling system 900 is shown and described with respect to a rotary drill system in FIG. 9, those skilled in the art will readily appreciate that many types of drilling systems can be employed in carrying out embodiments of the disclosure. For instance, drills and drill rigs used in embodiments of the disclosure may be used onshore (as depicted in FIG. 9) or offshore (not shown). Offshore oil rigs that may be used in accordance with embodiments of the disclosure include, for example, floaters, fixed platforms, gravity-based structures, drill ships, semi-submersible platforms, jack-up drilling rigs, tension-leg platforms, and the like. It will be appreciated that embodiments of the disclosure can be applied to rigs ranging anywhere from small in size and portable, to bulky and permanent. Further, although described herein with respect to oil drilling, various embodiments of the disclosure may be used in many other applications. For example, disclosed methods can be used in drilling for mineral exploration, environmental investigation, natural gas extraction, underground installation, mining operations, water wells, geothermal wells, and the like. Further, embodiments of the disclosure may be used in weight-on-packers assemblies, in running liner hangers, in running completion strings, etc., without departing from the scope of the disclosure.

Figure 10:
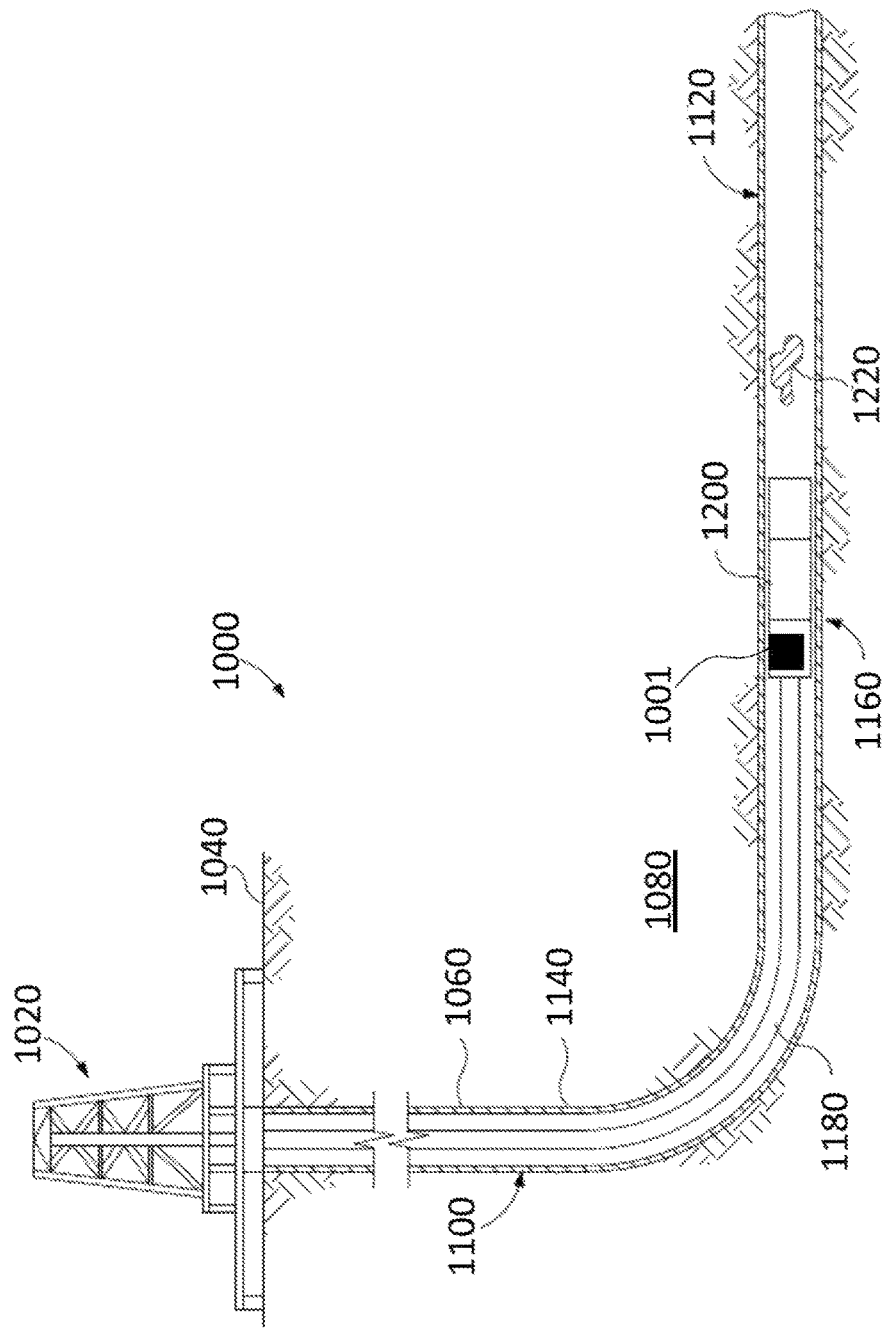
FIG. 10 illustrates a well system employing a sensor incorporating waveguides in a 3D substrate, according to some embodiments.

FIG. 10 illustrates a well system 1000 employing a sensor 1001 incorporating waveguides in a 3D substrate, according to some embodiments. Sensor 1001 may be the same as or similar to any one of sensors 100, 200*a*, 200*b* described in detail in FIG. 1 and in FIGS. 2A-B above. As illustrated, well system 1000 may include a service rig 1020 that is positioned on the earth's surface 1040 and extends over and around a wellbore 1060 that penetrates a subterranean formation 1080. Service rig 1020 may be a drilling rig, a completion rig, a workover rig, or the like. In some embodiments, service rig 1020 may be omitted and replaced with a standard surface wellhead completion or installation. Moreover, while well system 1000 is depicted as a land-based operation, it will be appreciated that the principles of the present disclosure could equally be applied in any sea-based or sub-sea application where service rig 1020 may be a floating platform or sub-surface wellhead installation, as generally known in the art.

Wellbore 1060 may be drilled into subterranean formation 1080 using any suitable drilling technique and may extend in a substantially vertical direction away from the earth's surface 1040 over a vertical wellbore portion 1100. At some point in wellbore 1060, vertical wellbore portion 1100 may deviate from vertical relative to the earth's surface 1040 and transition into a substantially horizontal wellbore portion 1120. In some embodiments, wellbore 1060 may be completed by cementing a casing string 1140 within wellbore 1060 along all or a portion thereof. As used herein, "casing string" may refer to any downhole tubular or string of tubulars known to those skilled in the art including, but not limited to, wellbore liner, production tubing, drill string, and other downhole piping systems.

System 1000 may further include a downhole tool 1160 conveyed into wellbore 1060. Downhole tool 1160 may be coupled or otherwise attached to a conveyance 1180 that extends from service rig 1020. Conveyance 1180 may be, but is not limited to, a wireline, a slickline, an electric line, coiled tubing, or the like. In some embodiments, device 1160 may be pumped downhole to a target location within wellbore 1060 using hydraulic pressure applied from service rig 1020 at surface 1040. In some embodiments, downhole tool 1160 may be conveyed to the target location using gravitational or otherwise natural forces. Downhole tool 1160 can be semi-permanently mounted with various measurement devices such as sensor 1001. In some embodiments, conveyance 1180 may include a fiber optic cable coupling a light source at surface 1040 to sensor 1001 (e.g., light source 102, cf. FIG. 1). The fiber optic cable may be configured to convey electromagnetic radiation to sensor 1001 (e.g., electromagnetic radiation 110*s* and electromagnetic radiation 110*r*, cf. FIG. 1).

Even though FIG. 10 depicts downhole tool 1160 as being arranged and operating in horizontal portion 1120, embodiments disclosed herein are equally applicable for use in portions of wellbore 1060 that are vertical, deviated, or otherwise slanted. Moreover, use of directional terms such as above, below, upper, lower, upward, downward, uphole, downhole, and the like are used in relation to the illustrative embodiments as they are depicted in the figures, the upward direction being toward the top of the corresponding figure and the downward direction being toward the bottom of the corresponding figure, the uphole direction being toward the surface of the well and the downhole direction being toward the toe of the well.

Those skilled in the art will readily appreciate that the methods described herein, or large portions thereof, may be automated at some point such that a computerized system may be programmed to design, predict, and devices that are more robust for compact optical systems operating in extreme environments. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A sensor for measuring a characteristic of a substance that includes a substrate having a cross-section and a length, a plurality of waveguides embedded in the substrate, the substrate providing an exposed surface, the exposed surface comprising a portion of a side surface of at least one of the plurality of waveguides, and a sensitized coating positioned on the exposed surface of the at least one of the plurality of waveguides.

B. A method for fabricating a sensor that includes forming a substrate in a three-dimensional shape, arranging at least two waveguides on an exposed surface of the substrate, applying a sensitive coating on an exposed side of one of the at least two waveguides, the exposed side being adjacent the exposed surface, and disposing a detector at a selected position relative to an optical output of each of the at least two waveguides.

C. A method for measuring a characteristic of a substance that includes exposing a surface of a sensor to the substance, the sensor including a substrate, a plurality of waveguides embedded in the substrate, and a sensitized coating positioned on a portion of at least one of the plurality of waveguides, directing a first portion of light through a first waveguide of the plurality of waveguides and thereby generating a first output signal, directing a second portion of light through a second waveguide of the plurality of waveguides and thereby generating a second output signal, obtaining a phase relation between the first portion of light and the second portion of light at an output of the first and second waveguides, generating an interference signal by combining the first and second output signals, detecting at least a portion of the interference signal with a detector, and determining the characteristic of the substance based on a change in a feature of the interference signal detected with the detector.

Each of embodiments A, B, and C may have one or more of the following additional elements in any combination: Element 1: wherein the exposed surface is curved in a direction perpendicular to a light propagation in the waveguide. Element 2: further comprising a detector arranged to receive an interference pattern generated from two waveguides of the plurality of waveguides, and configured to generate a signal corresponding to a change in an interference pattern, the change in the interference pattern induced by the characteristic of the substance. Element 3: wherein the interference pattern is formed in a free space between the detector an optical output of the waveguides. Element 4: wherein the sensitized coating comprises one of a chemically sensitive layer, a biologically sensitive layer, a hydrophilic layer, or a hydrophobic layer. Element 5: wherein the plurality of waveguides comprise a sample waveguide having the sensitized coating positioned thereon and being optically coupled with a signal electromagnetic radiation portion, a reference waveguide adjacent the sample waveguide and being optically coupled with a reference electromagnetic radiation portion, the reference radiation having a determined phase relation with the sample radiation. Element 6: further comprising a second sample waveguide being optically coupled with a second signal electromagnetic radiation portion, wherein the second signal electromagnetic radiation portion has a determined phase relation with the reference electromagnetic radiation portion. Element 7: further comprising a mask applied to the substrate to prevent background radiation in the substrate from reaching a detector. Element 8: wherein the sensitized coating targets one of the group consisting of water, gas, oil, methane, a hydrocarbon, a unicellular microorganism, an iron ion, and an alkali metal. Element 9: wherein the plurality of waveguides include at least a sample waveguide and a reference waveguide, the sensor further comprising a detector array to measure at least a portion of an interference pattern generated by the sample waveguide and the reference waveguide. Element 10: wherein the sensitized coating is configured to contact a substance including a target analyte. Element 11: wherein the substrate is cylindrical and the exposed surface is positioned at an inner diameter of the substrate.

Element 12: further comprising disposing a mask on a surface of the substrate that faces the detector. Element 13: further comprising heating and drawing the substrate to reduce an outer diameter (OD) of the waveguide structure. Element 14: wherein the at least two waveguides include a sample waveguide and a reference waveguide, the method further comprising determining an interference pattern for light emerging from the sample waveguide and the reference waveguide to select a position for disposing the detector. Element 15: further comprising overlapping a sensitive area of the detector with at least one of a peak of the interference pattern, a dark node of the interference pattern, and a portion of a peak and a dark node of the interference pattern.

Element 16: wherein exposing the sensitive surface of the sensor comprises allowing a target analyte to reach equilibrium on the sensitive surface of the sensor. Element 17: wherein obtaining a phase relation between the first portion of light and the second portion of light comprises splitting a light beam from a light source into the first portion of light and the second portion of light with a phase-preserving beam splitter element. Element 18: wherein detecting the interference signal with the detector comprises detecting a portion of the interference signal comprising at least one of a peak, a dark node, or a portion of a peak and a dark node. Element 19: wherein detecting the interference signal with the detector comprises coupling at least a portion of the interference signal to an optical fiber and transmitting the coupled portion to a remotely located detector. Element 20: wherein obtaining a phase relation between the first portion of light and the second portion of light comprises illuminating the first and second waveguides with a collimated and coherent light. Element 21: wherein determining the characteristic of the substance comprises finding the characteristic of the substance in a lookup table having a list of characteristics of the substance and a list of changes in interference signal values. Element 22: wherein determining the characteristic of the substance comprises determining at least one of a water concentration, a gas concentration, an oil concentration, a water-to-oil ratio, a methane concentration, or a hydrocarbon concentration, a unicellular microorganism presence or a unicellular microorganism concentration.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of fabricating a sensor, the method comprising:
    arranging at least two waveguides on an exposed surface of a three-dimensional substrate;
    applying a sensitive coating on an exposed side of one of the at least two waveguides along a longitudinal axis of the sensor, the exposed side being adjacent to the exposed surface; and
    disposing a mask on a surface of the three-dimensional substrate that is orthogonal to the longitudinal axis of the sensor, the mask being in contact with transparent portions of the three-dimensional substrate and the at least two waveguides.

2. The method of claim 1, further comprising:
    heating and drawing the three-dimensional substrate to reduce an outer diameter (OD) of the at least two waveguides.

3. The method of claim 1, further comprising:
    disposing a detector at a selected position relative to an optical output of each of the at least two waveguides.

4. The method of claim 3, wherein the at least two waveguides include a sample waveguide and a reference waveguide, the method further comprising determining an interference pattern for light emerging from the sample waveguide and the reference waveguide to select a position for disposing the detector.

5. The method of claim 4, further comprising:
    overlapping a sensitive area of the detector with at least one of a peak of the interference pattern, a dark node of the interference pattern, and a portion of a peak and a dark node of the interference pattern.

6. The method of claim 1, wherein the exposed surface is curved in a direction perpendicular to a light propagation in the at least two waveguides.

7. The method of claim 1, wherein the sensitized coating comprises one of a chemically sensitive layer, a biologically sensitive layer, a hydrophilic layer, or a hydrophobic layer.

8. The method of claim 1, wherein the arranging the at least two waveguides comprises:
    arranging a sample waveguide having the sensitized coating for optically coupling with a signal electromagnetic radiation; and
    arranging a reference waveguide adjacent to the sample waveguide for optically coupling with a reference electromagnetic radiation, the reference electromagnetic radiation having a determined phase relation with the signal electromagnetic radiation.

9. A method of fabricating a sensor for measuring a characteristic of a substance, comprising:
    arranging a plurality of sensing channels along an exposed surface of a substrate, each of the plurality of sensing channels comprising a plurality of waveguides embedded in the substrate, wherein a first group of sensing channels of the plurality of sensing channels share a first reference waveguide of the plurality of waveguides and a second group of sensing channels of the plurality of sensing channels share a second reference waveguide of the plurality of waveguides, the first reference waveguide being different from the second reference waveguide, the exposed surface comprising a portion of a side surface of at least one of the plurality of waveguides;
    applying a sensitized coating on the exposed surface of the at least one of the plurality of waveguides along a longitudinal axis of the sensor; and
    disposing a mask on a surface of the substrate that is orthogonal to the longitudinal axis of the sensor, the mask being in contact with transparent portions of the substrate and the plurality of waveguides.

10. The method of claim 9, wherein the exposed surface is curved in a direction perpendicular to a light propagation in the waveguide.

11. The method of claim 9, further comprising:
    arranging a detector to receive an interference pattern generated from two waveguides of the plurality of waveguides, the detector being configured to generate a signal corresponding to a change in an interference pattern, the change in the interference pattern induced by the characteristic of the substance.

12. The method of claim 11, wherein the interference pattern is formed in a free space between the detector and an optical output of the plurality of waveguides.

13. The method of claim 9, wherein the sensitized coating comprises one of a chemically sensitive layer, a biologically sensitive layer, a hydrophilic layer, or a hydrophobic layer.

14. The method of claim 9, wherein the arranging the plurality of sensing channels comprises:
    arranging a sample waveguide having the sensitized coating for optically coupling with a signal electromagnetic radiation; and
    arranging a reference waveguide adjacent to the sample waveguide for optically coupling with a reference electromagnetic radiation, wherein the reference electromagnetic radiation has a determined phase relation with the signal electromagnetic radiation.

15. The method of claim 14, further comprising:
    arranging a second sample waveguide for optically coupling with a second signal electromagnetic radiation, wherein the second signal electromagnetic radiation has a determined phase relation with the reference electromagnetic radiation.

16. The method of claim 9, wherein the mask is disposed on the substrate to prevent background radiation in the substrate from reaching a detector.

17. The method of claim 9, wherein the sensitized coating targets one of a group consisting of water, gas, oil, methane, a hydrocarbon, a unicellular microorganism, an iron ion, and an alkali metal.

18. The method of claim 9, wherein the arranging the plurality of sensing channels comprises:
arranging at least a sample waveguide and a reference waveguide, wherein the method further comprises:
arranging a detector array to measure at least a portion of an interference pattern generated by the sample waveguide and the reference waveguide.

19. The method of claim 9, wherein the sensitized coating is configured to contact a substance including a target analyte.

20. The method of claim 9, wherein the substrate is cylindrical and the exposed surface is positioned at an inner diameter of the substrate.

\* \* \* \* \*